US012702376B2

(12) United States Patent
Lu et al.

(10) Patent No.: US 12,702,376 B2
(45) Date of Patent: Aug. 11, 2026

(54) METHOD AND APPARATUS FOR PERFORMING AUTOMATIC EXPOSURE CONTROL IN CT IMAGING SYSTEMS

(71) Applicant: Canon Kabushiki Kaisha, Tokyo (JP)

(72) Inventors: Yujie Lu, Vernon Hills, IL (US); Ting Xia, Vernon Hills, IL (US); Jian Zhou, Vernon Hills, IL (US); Liang Cai, Vernon Hills, IL (US)

(73) Assignee: Canon Kabushiki Kaisha, Tokyo (JP)

( * ) Notice: Subject to any disclaimer, the term of this patent is extended or adjusted under 35 U.S.C. 154(b) by 106 days.

(21) Appl. No.: 18/829,932

(22) Filed: Sep. 10, 2024

(65) Prior Publication Data

US 2026/0069234 A1 Mar. 12, 2026

(51) Int. Cl.

*A61B 6/02* (2006.01)
*A61B 6/00* (2006.01)
*A61B 6/03* (2006.01)
*A61B 6/40* (2024.01)

(52) U.S. Cl.

CPC .............. *A61B 6/542* (2013.01); *A61B 6/027* (2013.01); *A61B 6/032* (2013.01); *A61B 6/405* (2013.01); *A61B 6/488* (2013.01); *A61B 6/5205* (2013.01)

(58) Field of Classification Search

CPC ......... A61B 6/542; A61B 6/027; A61B 6/032; A61B 6/405; A61B 6/488; A61B 6/5205

See application file for complete search history.

(56) References Cited

U.S. PATENT DOCUMENTS 9,865,060 B2 1/2018 Mukumoto
10,945,697 B2 3/2021 Goto et al.
2009/0122952 A1* 5/2009 Nishide ................. A61B 6/542 378/4
2010/0226474 A1* 9/2010 Yamakawa ........... A61B 6/482 378/5

(Continued)

OTHER PUBLICATIONS

Sookpeng et al., "Comparison of different phantom designs for CT scanner automatic tube current modulation system tests", Journal of Radiological Protection, 33, 2013, pp. 735-761.

(Continued)

*Primary Examiner* — Uzma Alam
*Assistant Examiner* — Mamadou Faye
(74) *Attorney, Agent, or Firm* — Oblon, McClelland, Maier & Neustadt, L.L.P.

(57) ABSTRACT

An apparatus for performing automatic exposure control in a computed tomography (CT) imaging system including an X-ray source is provided. The apparatus includes processing circuitry configured to acquire helical scan data from a scout scan performed on a first imaging object, determine a target noise standard deviation (STD) for an imaging scan to be performed on the first imaging object after the scout scan, retrieve a pre-stored attenuation-noise-dose relationship relating attenuation of X-rays from the X-ray source that pass through a second imaging object, noise present in reconstructed images of the second imaging object, and tube current values applied to the X-ray source, use the acquired helical scan data and the determined target noise STD to generate a tube current modulation curve, based on the retrieved attenuation-noise-dose relationship, and perform the imaging scan on the first imaging object using the generated tube current modulation curve.

20 Claims, 12 Drawing Sheets

(56) References Cited

U.S. PATENT DOCUMENTS

| | | | |
|---|---|---|---|
| 2023/0080631 | A1 | 3/2023 | Wang et al. |
| 2023/0274475 | A1 | 8/2023 | Yan et al. |
| 2023/0284997 | A1 | 9/2023 | Xia et al. |

OTHER PUBLICATIONS

Mussmann et al., "Organ-based tube current modulation in chest CT. A comparison of three vendors", Radiography, 2020, 7 pages.

Klein et al., "Patient-specific radiation risk-based tube current modulation for diagnostic CT", Medical Physics, 2022, pp. 4391-4403.

* cited by examiner

METHOD AND APPARATUS FOR PERFORMING AUTOMATIC EXPOSURE CONTROL IN CT IMAGING SYSTEMS

BACKGROUND

Field

This disclosure relates to X-ray computed tomography (CT) imaging systems.

Description of the Related Art

Computed tomography (CT) scans use ionizing radiation to create images of patients' bodies, which can increase the risk of developing cancer later in life. It has been reported that CT contributes the highest collective amount of medical radiation exposure in the United States compared with any other medical imaging modality.

When conducting diagnostic CT imaging, depending on different protocols, different anatomies of the body may require different exposures. It is ideal to scan patients with minimized dose while keeping image quality at a clinically acceptable level. However, dose reduction often leads to a low signal-to-noise ratio (SNR), potentially affecting the detectability of certain structures or pathologies.

To address this problem, one effective approach in CT imaging is the modulation of X-ray tube current, known as automatic exposure control (AEC). AEC aims to automatically optimize CT scan exposures, ensuring reduced radiation dose to the body while keeping consistent image quality, so as to simplify radiologists' workflow. This strategy has found widespread application across various protocols and anatomical regions in routine clinical scans.

Almost all CT vendors now offer AEC functionality in clinical scans. Recent advancements have introduced organ-based tube current modulation to mitigate radiation exposure to sensitive organs. However, the current AEC approach usually relied on 2D radiographic images (typically one or two projection views), leading to limited predictive accuracy. Additionally, variations in patient size, anatomy, and location within the CT scanner during scanning further increase the difficulty of AEC prediction. As a result, achieving precise AEC is still a challenging problem especially for patient-specific scans.

It is desirable to develop an AEC prediction approach that can provide more accurate and comprehensive tomographic image information.

SUMMARY

The present disclosure relates to an apparatus for performing automatic exposure control in a computed tomography (CT) imaging system including an X-ray source. The apparatus includes processing circuitry configured to acquire helical scan data from a scout scan performed on a first imaging object, determine a target noise standard deviation (STD) for an imaging scan to be performed on the first imaging object after the scout scan, retrieve a pre-stored attenuation-noise-dose relationship relating attenuation of X-rays from the X-ray source that pass through a second imaging object, noise present in reconstructed images of the second imaging object, and tube current values applied to the X-ray source, use the acquired helical scan data and the determined target noise STD to generate a tube current modulation curve, based on the retrieved attenuation-noise-dose relationship, and perform the imaging scan on the first imaging object using the generated tube current modulation curve.

The disclosure additionally relates to a method for performing X-ray exposure control in a CT imaging system including an X-ray source. The method includes acquiring helical scan data from a scout scan performed on a first imaging object, determining a target noise STD for an imaging scan to be performed on the first imaging object after the scout scan, retrieving a pre-stored attenuation-noise-dose relationship relating attenuation of X-rays from the X-ray source that pass through a second imaging object, noise present in reconstructed images of the second imaging object, and tube current values applied to the X-ray source, using the acquired helical scan data and the determined target noise STD to generate a tube current modulation curve, based on the retrieved attenuation-noise-dose relationship, and performing the imaging scan on the first imaging object using the generated tube current modulation curve.

The disclosure additionally relates to a non-transitory computer readable medium having instructions stored therein that, when executed by one or more processors, cause the one or more processors to perform the above-described method for performing X-ray exposure control in a CT imaging system including an X-ray source.

Note that this summary section does not specify every embodiment and/or incrementally novel aspect of the present disclosure or claimed invention. Instead, the summary only provides a preliminary discussion of different embodiments and corresponding points of novelty. For additional details and/or possible perspectives of the invention and embodiments, the reader is directed to the Detailed Description section and corresponding figures of the present disclosure as further discussed below.

BRIEF DESCRIPTION OF THE DRAWINGS

Various embodiments of this disclosure that are proposed as examples will be described in detail with reference to the following figures, wherein like numerals reference like elements, and wherein.

DETAILED DESCRIPTION

The following disclosure provides embodiments or examples for implementing different features of the provided subject matter. Specific examples of components and arrangements are described below to simplify the present disclosure. These are, of course, merely examples and are not intended to be limiting.

For example, the order of discussion of the different steps as described herein has been presented for the sake of clarity. In general, these steps can be performed in any suitable order. Additionally, although each of the different features, techniques, configurations, etc. herein may be discussed in different places of this disclosure, it is intended that each of the concepts can be executed independently of each other or in combination with each other. Accordingly, the present invention can be embodied and viewed in many different ways.

Furthermore, as used herein, the words "a," "an," and the like generally carry a meaning of "one or more," unless stated otherwise.

The present disclosure provides a method and apparatus aimed at improving automatic explore control (AEC) accuracy and thereby enhancing the image quality of computed tomography (CT) imaging systems. Typically, the patient data available prior to a normal scan is limited. This limitation poses a challenge for precise AEC prediction, as current methods rely on a model using 2D patient information acquired pre-acquisition. In contrast, the method and apparatus provided in the disclosure utilize an AEC prediction framework based on patient information obtained from a 3D scout scan. By establishing an anatomy-oriented relationship among attenuation, image noise, and dose levels, this AEC prediction framework can provide more accurate and efficient AEC predictions.

Figure 1:
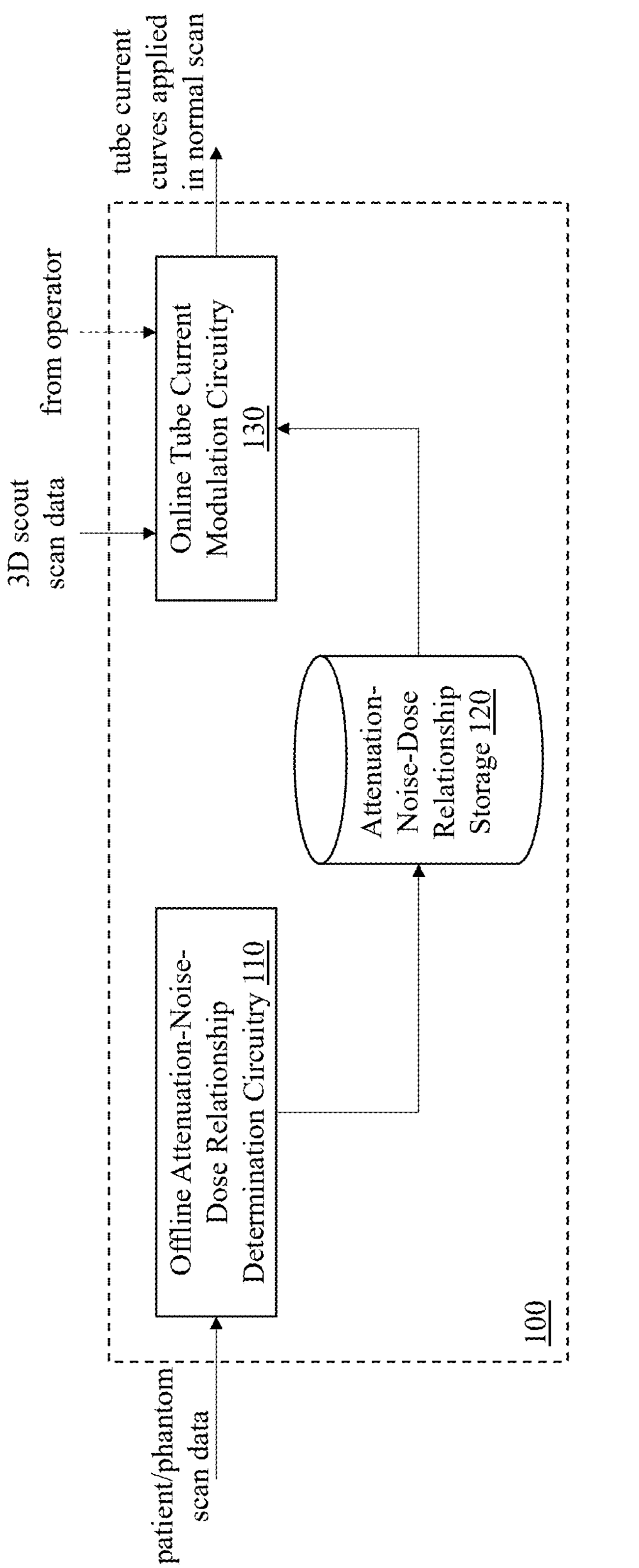
FIG. 1 shows a block diagram of an exemplary apparatus for performing automatic exposure control (AEC) in a computed tomography (CT) imaging system in accordance with embodiments of the disclosure.

FIG. 1 shows a block diagram of an exemplary apparatus for performing AEC in a CT imaging system in accordance with embodiments of the disclosure. The apparatus 100 includes offline attenuation-noise-dose relationship determination circuitry 110, attenuation-noise-dose relationship storage 120, and online tube current modulation circuitry 130.

The offline attenuation-noise-dose relationship determination circuitry 110 gathers helical scan data from scans conducted on patients and/or phantoms at various dose levels (i.e., various tube current values applied to an X-ray source of the CT imaging system), and uses the gathered data to develop an attenuation-noise-dose relationship for each anatomical region, such as the head, head/neck, shoulder, lung, abdomen, pelvis, etc. Once developed, these anatomy-specific relationships can be stored in the attenuation-noise-dose relationship storage 120.

The online tube current modulation circuitry 130 acquires helical scan data generated from a 3D scout scan performed on a patient, and retrieves the attenuation-noise-dose relationships stored in the attenuation-noise-dose relationship storage 120. The online tube current modulation circuitry 130 also obtains a target noise standard deviation (STD) for a normal scan to be performed on the patient after the 3D scout scan. For example, the target noise STD can be received from an operator of the CT imaging system. Using the scout scan data and the target noise STD, the online tube current modulation circuitry 130 can generate a tube current curve for each anatomical region, based on the attenuation-noise-dose relationships. Then, the generated tube current curves can be applied during the normal scan to facilitate automatic tube current modulation.

Figure 2:
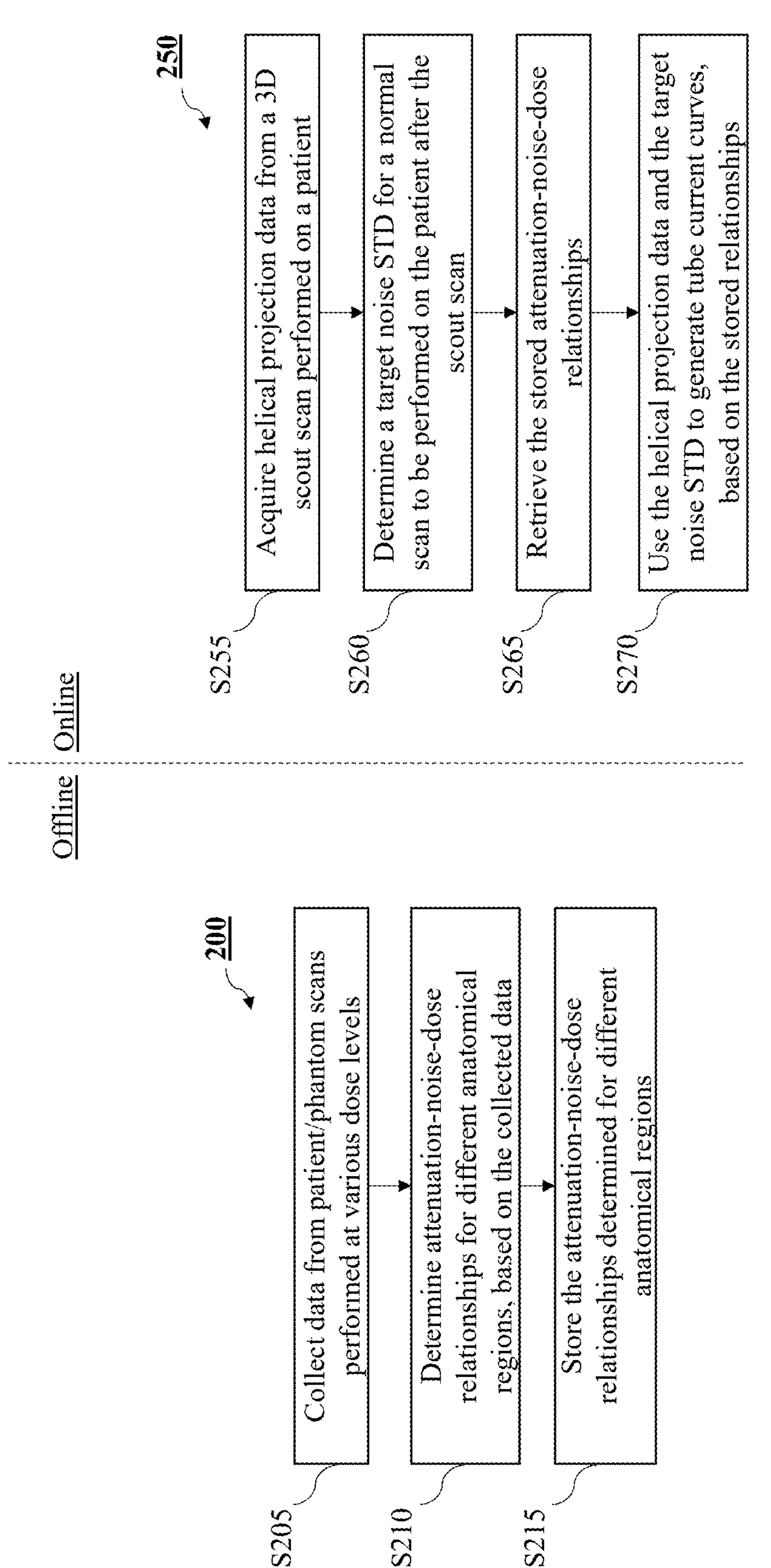
FIG. 2 shows a flow chart of an exemplary procedure for performing AEC in a CT imaging system in accordance with embodiments of the disclosure.

FIG. 2 shows a flow chart of an exemplary procedure for implementing AEC in a CT imaging system in accordance with embodiments of the disclosure. As illustrated in FIG. 2, the AEC procedure includes an offline portion 200 for establishing the attenuation-noise-dose relationships and an online part 250 for applying the attenuation-noise-dose relationships to conduct tube current modulation prediction.

The offline procedure 200 starts at step S205 by collecting data from patient/phantom scans performed across a range of dose levels. In step S210, attenuation-noise-dose relationships are determined for different anatomical regions based on the collected data. In step S215, the determined attenuation-noise-dose relationships are stored in the attenuation-noise-dose relationship storage 120 for use in the online procedure 250.

The online procedure 250 can be conducted on patients in real-time to apply the stored attenuation-noise-dose relationships for automatic tube current modulation. In step S255, helical projection data is acquired from a 3D scout scan performed on a patient. In step S260, a target noise STD for a normal scan to be performed on the patient is determined. In step S265, the stored attenuation-noise-dose relationships are retrieved. In step S270, using the target noise STD and the helical projection data, tube current curves are generated for various anatomical regions, based on the attenuation-noise-dose relationships. The generated tub current curves can be applied in automatic tube current modulation during the normal scan conducted on the patient.

Figure 3:
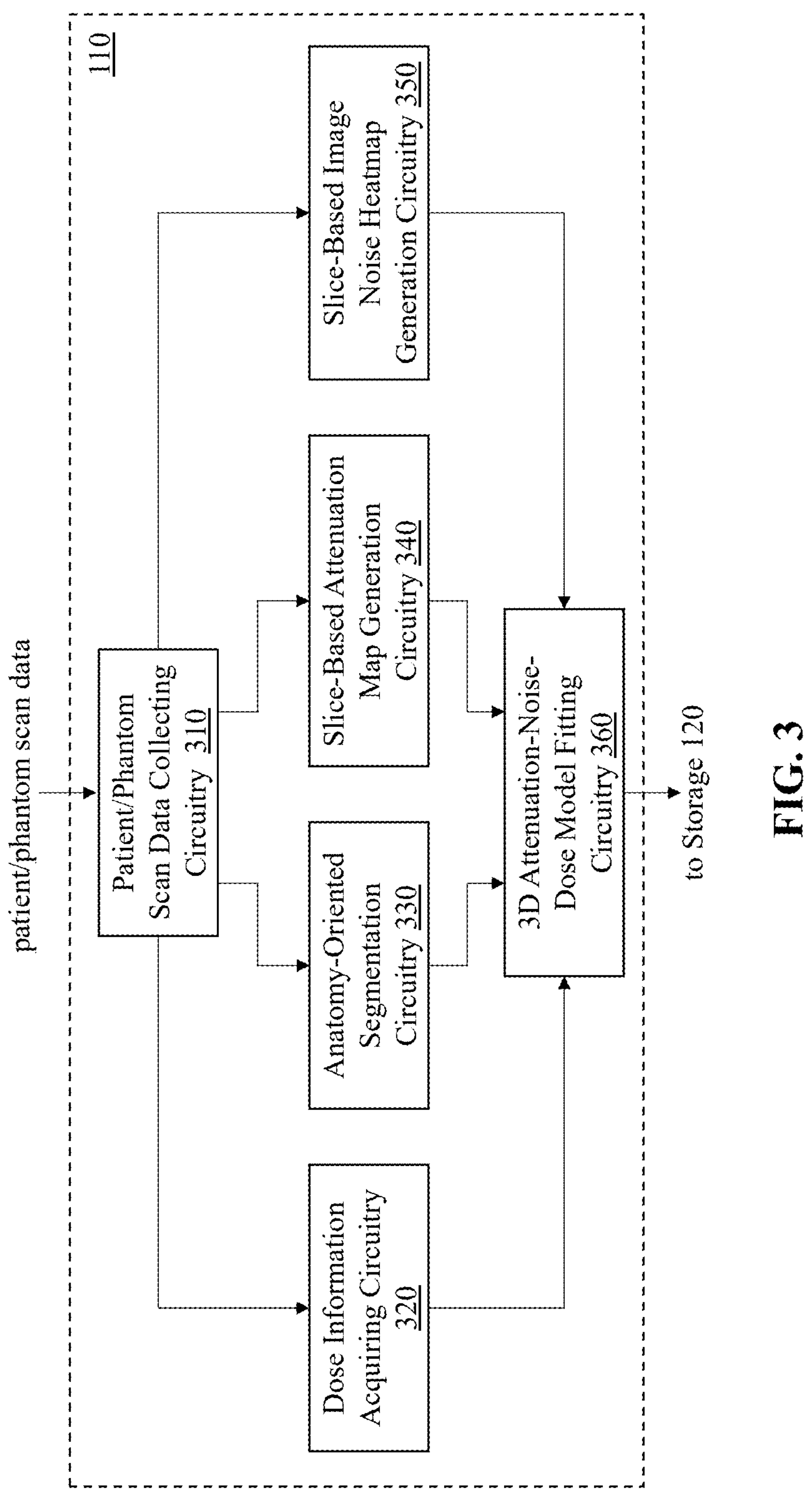
FIG. 3 shows a block diagram of offline attenuation-noise-dose relationship determination circuitry in accordance with embodiments of the disclosure.

FIG. 3 shows a block diagram of the offline attenuation-noise-dose relationship determination circuitry 110 in accordance with embodiments of the disclosure. The offline attenuation-noise-dose relationship determination circuitry 110 includes patient/phantom scan data collecting circuitry 310, dose information acquiring circuitry 320, anatomy-oriented segmentation circuitry 330, slice-based attenuation map generation circuitry 340, slice-based image noise heatmap generation circuitry 350, and 3D attenuation-noise-dose model fitting circuitry 360.

The patient/phantom scan data collecting circuitry 310 collects data from scans performed on one or more patients and/or phantoms at various dose levels. From the data collected by the patient/phantom scan data collecting circuitry 310, the dose information acquiring circuitry 320 extracts information regarding the dose levels used during the patient/phantom scans and sends this dose information to the 3D attenuation-noise-dose model fitting circuitry 360.

The anatomy-oriented segmentation circuitry 330 receives the scan data from the patient/phantom scan data collecting circuitry 310, performs anatomy-oriented segmentation based on the received scan data, and sends the segmentation results to the 3D attenuation-noise-dose model fitting circuitry 360.

As previously noted, different anatomies of the body may require different exposure levels. Moreover, variations in anatomical structures and sizes can result in different attenuations and affect the noise STD. To take into account these differences across anatomical regions, the AEC framework provided in this disclosure adopts an anatomy-oriented segmentation method. This approach can improve the accuracy of AEC prediction by accommodating the unique characteristics of different anatomies.

In one embodiment of the disclosure, deep learning techniques are used for the anatomy-oriented segmentation. For instance, a neural network including three-dimensional convolutions can learn segmentation through supervised training. A typical U-net and other suitable network architectures can be used to implement this neural network.

For example, the training dataset can include image volumes from helical scans conducted on various patients and phantoms. The training target for the neural network is segmented labels corresponding to different anatomies. Manual segmentation can be used to differentiate the various anatomical regions. The loss function can be selected based on optimized training results.

Figure 4:
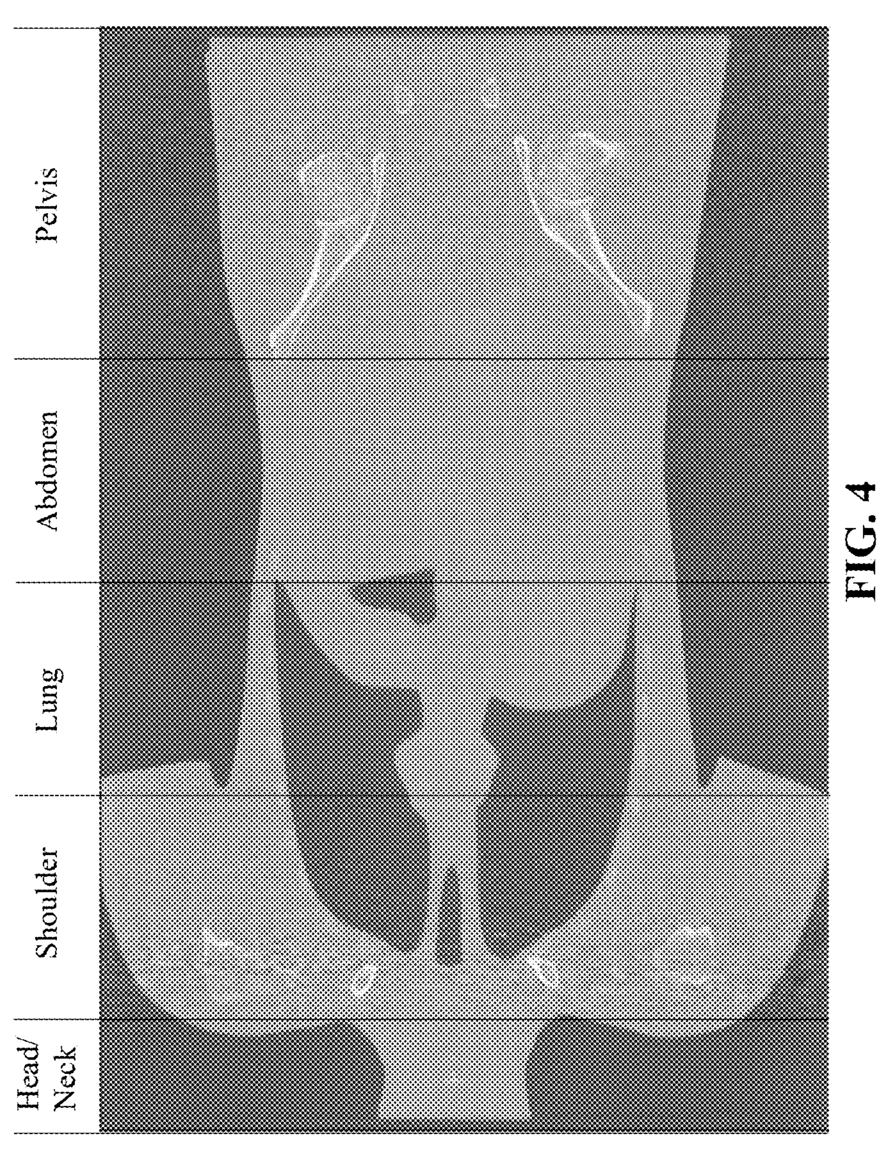
FIG. 4 shows exemplary anatomical segmentation along the longitudinal direction in accordance with embodiments of the disclosure.

An exemplary segmentation generated using a body phantom CT images along the longitudinal direction is shown in FIG. 4. Major parts can include the regions of head/neck, shoulder, lung, abdomen, and pelvis, for example.

Referring back to FIG. 3, the slice-based attenuation map generation circuitry 340 receives the scan data from the patient/phantom scan data collecting circuitry 310, uses the received data to generate an attenuation map slice by slice, and sends the generated attenuation maps to the 3D attenuation-noise-dose model fitting circuitry 360.

Various methods are available for generating attenuation maps in a slice-by-slice manner from raw CT projection data, including, but not limited to, the analytical reconstruction method. Additionally, a weighting scheme, such as Parker weights, can be used to deal with potential data redundancy in the raw projections. The attenuation maps are generated in the form of 2D reconstructed slices. Each pixel within a 2D reconstructed slice represents the measured linear attenuation coefficient ($\mu$) of a voxel within the corresponding patient/phantom.

The slice-based image noise heatmap generation circuitry 350 receives the scan data from the patient/phantom scan data collecting circuitry 310, generates an image noise heatmap in a slice-by-slice manner, and sends the image noise heatmaps to the 3D attenuation-noise dose model fitting circuitry 360.

Various methods can be used to obtain image noise, including deriving it from reconstructed images or from the noise present in projection data, for example.

Figure 5D:
FIGS. 5A-5D show an exemplary scenario depicting the generation of an image noise map from even and odd projection data in accordance with embodiments of the disclosure.
Figure 5D:
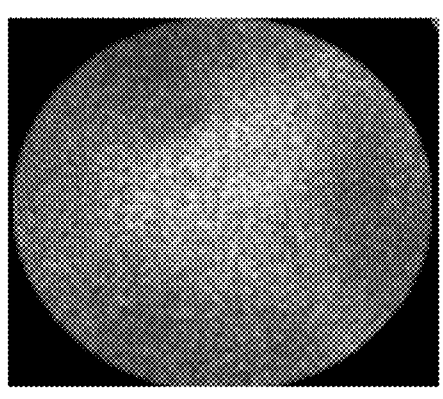
Figure 5C:
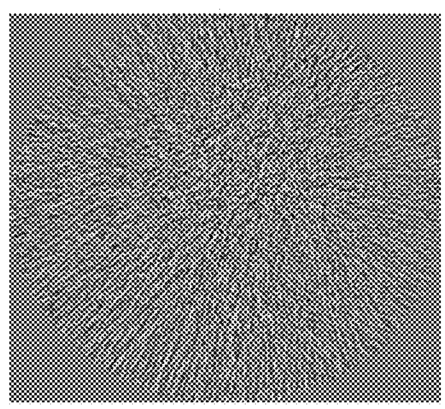
Figure 5B:
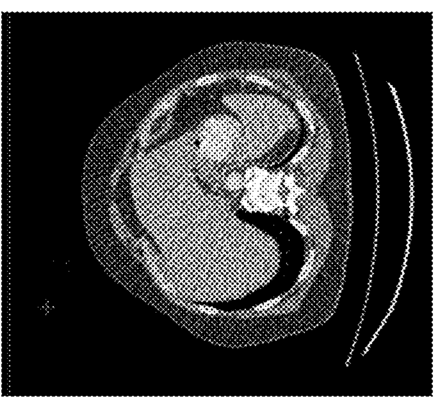
Figure 5A:

In one embodiment of the disclosure, the CT projection data is grouped into odd and even projections. The group of odd projections can be used to reconstruct one image (shown in FIG. 5A), while the group of even projections can be used to reconstruct another image (shown in FIG. 5B) that corresponds to the same slice. By subtracting one of the two reconstructed images from the other, a difference image can be obtained, as shown in FIG. 5C. Then, the difference image can be converted to a slice-specific noise heatmap (shown in FIG. 5D), which represents a distribution of noise within the slice.

Although the above embodiment uses a difference image obtained from two images reconstructed using even and odd projections, alternative grouping methods for projection data are feasible. For example, by randomly choosing one view from each consecutive pair of views and assigning it to a first group and assigning the other in the pair to a second group, two non-overlapping projection groups can be derived. In other examples, it can even be possible to allow a certain number of views to overlap between the two groups.

Referring back to FIG. 3, with respect to each anatomical region segmented by the anatomy-oriented segmentation circuitry 330, the 3D attenuation-noise-dose model fitting circuitry 360 can use the received dose information, attenuation maps, and image noise heatmaps to establish a 3D attenuation-noise-dose model. Specifically, coefficients of the 3D model are determined through model fitting to represent a correlation or relationship among attenuation, image noise, and dose levels that is specific to the anatomical region. These coefficients derived from the model fitting can then be saved in the attenuation-noise-dose relationship storage 120 for use in real-time AEC predictions.

Figure 6:
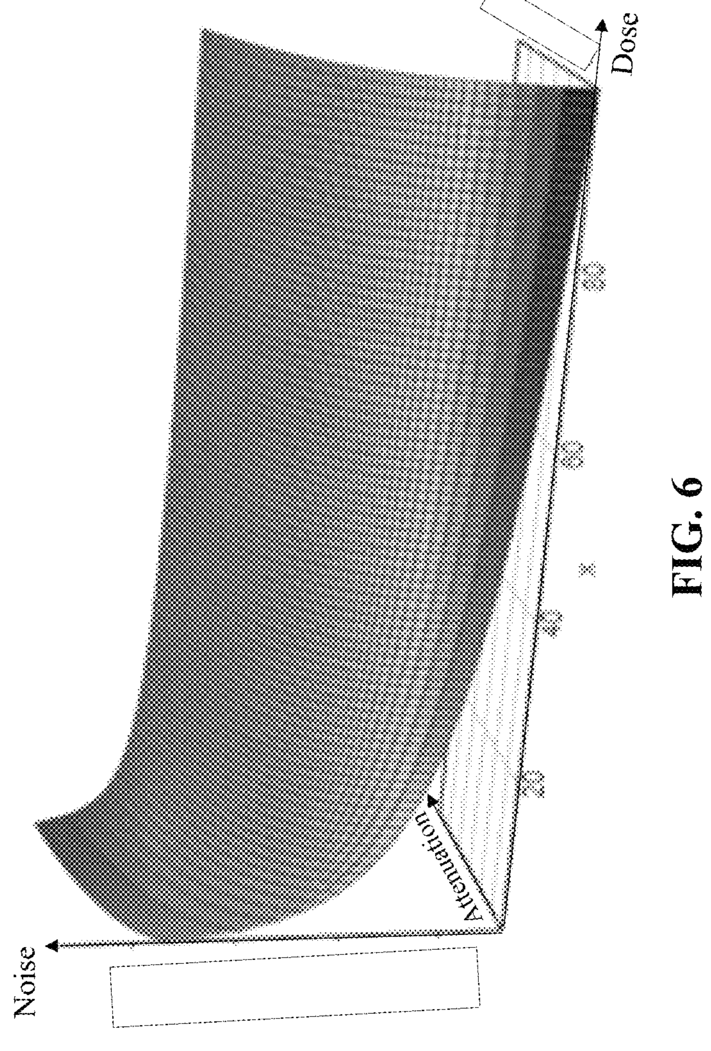
FIG. 6 shows an exemplary 3D surface representing the relationship between dose, image noise, and attenuation, in accordance with embodiments of the disclosure.

FIG. 6 shows an exemplary 3D surface representing the relationship among dose, image noise, and attenuation in accordance with embodiments of the disclosure. Contrasted with previous approaches that modulate the tube current based solely on noise distribution, incorporating the additional dimension of attenuation enhances the accuracy of AEC predictions.

Figure 7:
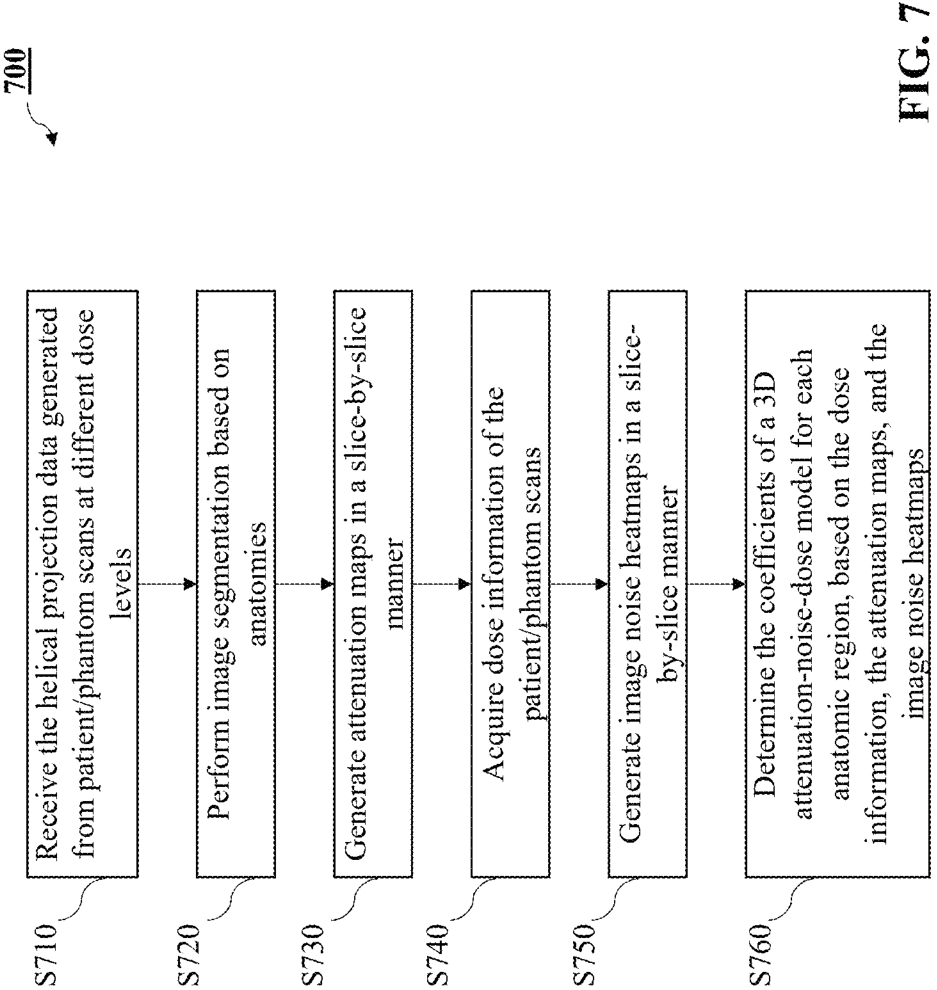
FIG. 7 shows a flow chart of an exemplary procedure for determining the attenuation-noise-dose relationship in accordance with embodiments of the disclosure.

FIG. 7 shows a flow chart of an exemplary procedure 700 for determining the attenuation-noise-dose relationships in accordance with embodiments of the disclosure. In step S710, the projection data generated from helical scans on patients and/or phantoms at different dose levels are received. In step S720, based on the received helical projection data, anatomy-oriented image segmentation is performed to obtain anatomical regions. In step S730, attenuation maps are generated in a slice-by-slice manner based on the received helical projection data. In step S740, dose information is obtained from the scan data. In step S750, image poise heatmaps are generated in a slice-by-slice manner based on the received helical projection data. In step S760, for each anatomic region, coefficients of a 3D attenuation-noise-dose model are determined for each anatomic region through model fitting based on the dose information, the attenuation maps, and the image noise heatmaps. These coefficients of the 3D model can be stored for use during the online tube current modulation procedure 250.

In the embodiment shown in FIGS. 3 and 7, coefficients of a 3D surface model are determined for each anatomical region to represent the correlation or relationship among attenuation, image noise, and dose levels. Alternatively, a look-up table can be created for each anatomical region to represent such correlation or relationship. For example, the look-up table include a plurality of entries associating anatomical regions with respective attenuation, noise, and dose levels.

Figure 8:
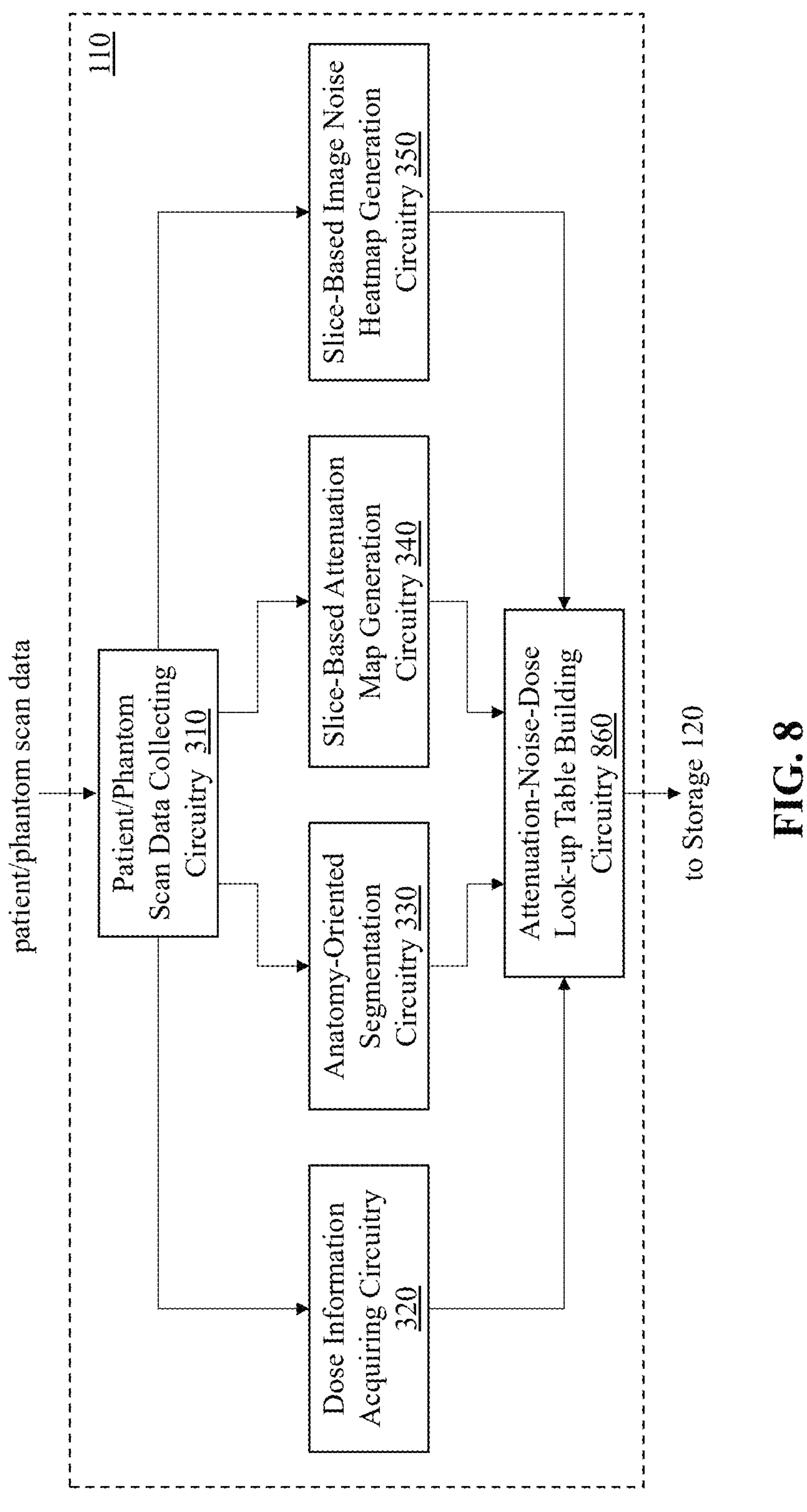
FIG. 8 shows a block diagram of offline attenuation-noise-dose relationship determination circuitry in accordance with embodiments of the disclosure.

FIG. 8 shows a block diagram of the offline attenuation-noise-dose relationship determination circuitry 110 in accordance with embodiments of the disclosure. The offline attenuation-noise-dose relationship determination circuitry 110 includes patient/phantom scan data collecting circuitry 310, dose information acquiring circuitry 320, anatomy-oriented segmentation circuitry 330, slice-based attenuation map generation circuitry 340, slice-based image noise heatmap generation circuitry 350, and attenuation-noise-dose look-up table building circuitry 860. In FIG. 8, the structures and functionalities of the patient/phantom scan data collecting circuitry 310, dose information acquiring circuitry 320, anatomy-oriented segmentation circuitry 330, slice-based attenuation map generation circuitry 340, slice-based image noise heatmap generation circuitry 350 are identical to those of the corresponding components in FIG. 3.

The attenuation-noise-dose look-up table building circuitry 860 receives the dose information acquired by the dose information acquiring circuitry 320, the anatomical regions segmented by the anatomy-oriented segmentation circuitry 330, the attenuation maps generated by the slice-based attenuation map generation circuitry 340, and the image noise heatmaps generated by the slice-based image noise heatmap generation circuitry 350. The attenuation-noise-dose look-up table building circuitry 360 use the received data to construct anatomy-specific look-up tables representing the correlation among, attenuation, image noise, and dose. The constructed look-up tables for the respective anatomical regions can then be saved in the storage 120 for use in real-time AEC predictions.

Note that the look-up tables can extend to include even more dimensions. For example, various factors affecting image noise, including, but not limited to, anatomical regions, attenuation, X-ray source voltage and current, wedge, helical pitches, etc., can be integrated into the look-up tables, resulting in a more comprehensive representation of the imaging environment.

Figure 9:
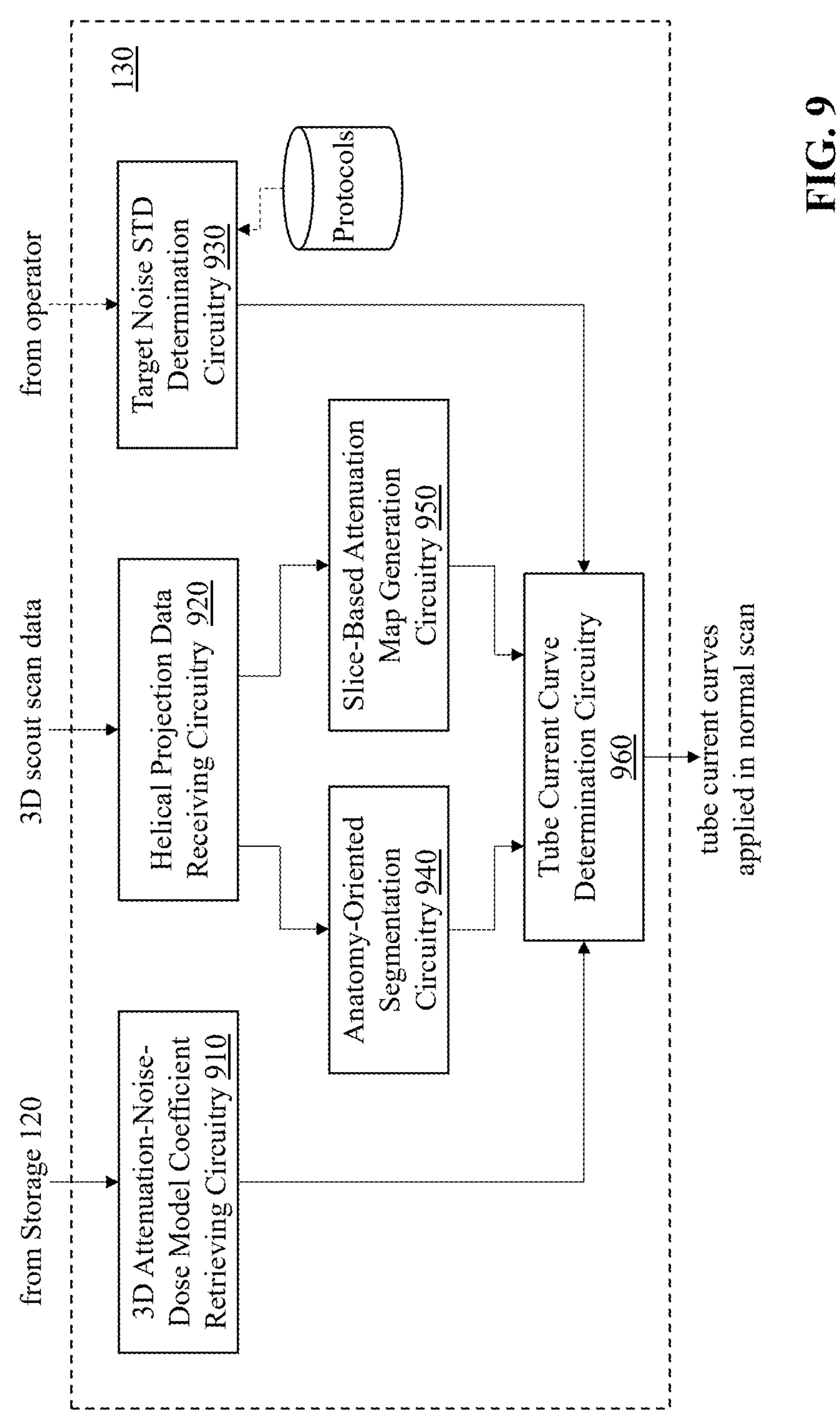
FIG. 9 shows a block diagram of online tube current modulation circuitry in accordance with embodiments of the disclosure.

FIG. 9 shows a block diagram of the online tube current modulation circuitry 130 in accordance with embodiments of the disclosure. The online tube current modulation circuitry 130 includes 3D attenuation-noise-dose model coefficient retrieving circuitry 910, helical projection data receiving circuitry 920, target noise STD determination circuitry 930, anatomy-oriented segmentation circuitry 940, slice-based attenuation map generation circuitry 950, and tube current curve determination circuitry 960.

The 3D attenuation-noise-dose model coefficient retrieving circuitry 910 retrieves the 3D model coefficients for various anatomical regions from the attenuation-noise-dose relationship storage 120, and sends the coefficients to the tube current curve determination circuitry 960.

The helical projection data receiving circuitry 920 receives helical projection data generated from the 3D scout scan on the patient, and sends the received data to the anatomy-oriented segmentation circuitry 940 and the slice-based attenuation map generation circuitry 950.

The target noise STD determination circuitry 930 determines a target noise STD for the normal scan to be performed on the patient after the scout scan, and sends the target noise STD to the tube current curve determination circuitry 960. For example, the target noise STD can be determined based on the protocol of the normal scan, or be decided by the operator of the CT scanner.

The anatomy-oriented segmentation circuitry 940 uses the received helical scan data to perform segmentation based on anatomical regions, and sends the segmentation results to the tube current curve determination circuitry 960. Similar to the anatomy-oriented segmentation circuitry 330 in FIGS. 3 and 8, the anatomy-oriented segmentation circuitry 940 can be realized through a trained neural network.

Based on the received helical scan data, the slice-based attenuation map generation circuitry 950 generates an attenuation map in a slice-by-slice manner, and sends the generated attenuation maps to the tube current curve determination circuitry 960. Similar to the slice-based attenuation map generation circuitry 340 in FIGS. 3 and 8, the slice-based attenuation map generation circuitry 950 can generate the attenuation maps through analytical reconstruction of raw projection data. Additionally, weighting schemes can be applied to handle potential data redundancy within the projection data.

Using the model coefficients received from the 3D attenuation-noise-dose model coefficient retrieving circuitry 910, the tube current curve determination circuitry 960 determines tube current curves for various anatomical regions, based on the received attenuation maps and target noise STD.

Figure 10:
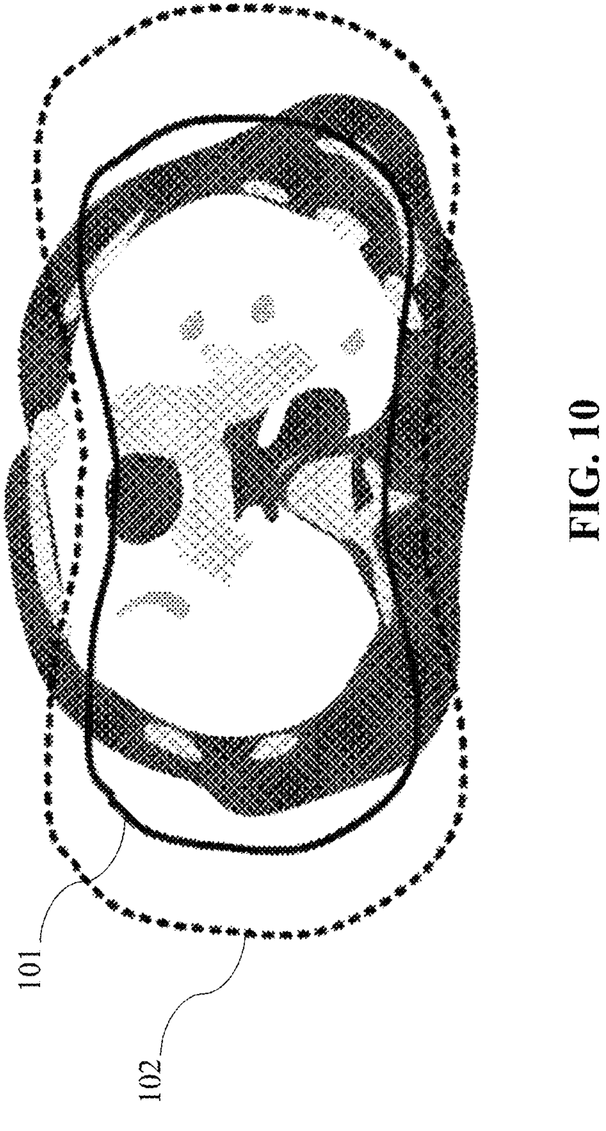
FIG. 10 shows exemplary tube current curves in accordance with embodiments of the disclosure.

FIG. 10 shows exemplary tube current curves in an axial cross-section of the lung area, in accordance with embodiments of the disclosure. The tube current value can be modulated on the basis of the specific tube current curve selected for the area. The distance of a tube current curve relative to the center illustrates the intensity of the tube current. Given that the tube current curve 101 has a shorter distance from the center than that of the tube current curve 102, the X-ray radiation applied to the lung area can be reduced by selecting the tube current curve 101. Moreover, as can be seen from the curve 101, the tube current reaches its maximum value in the lateral direction, and its minimum value in the anterior posterior (AP) direction.

Figure 11:
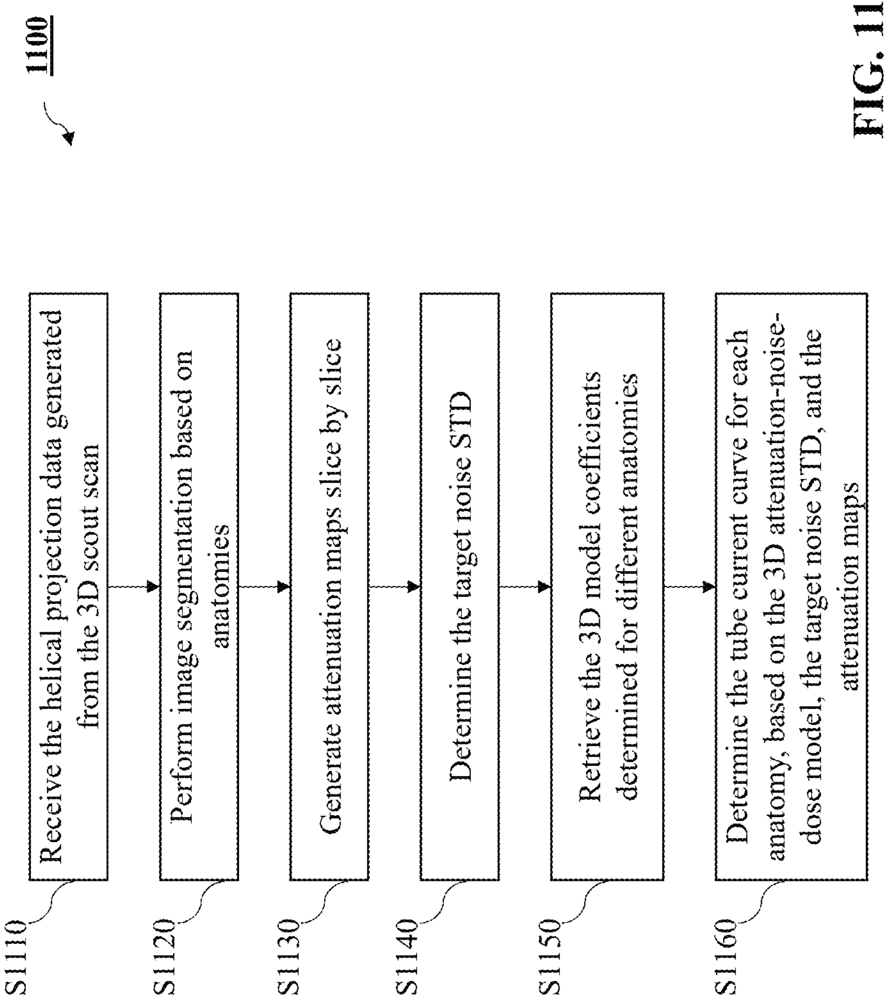
FIG. 11 shows a flow chart of an exemplary procedure for performing online tube current modulation in accordance with embodiments of the disclosure.

FIG. 11 shows a flow chart of an exemplary procedure for performing online tube current modulation in accordance with embodiments of the disclosure. In step S1110, the helical projection data generated from the 3D scout scan on the patient is received. In step S1120, anatomy-oriented image segmentation is performed on an image reconstructed from the helical projection data. In step S1130, attenuation maps are generated in a slice-by-slice manner based on the helical projection data. In step S1140, the target noise STD is determined for the normal scan to be performed on the patient. In step S1150, coefficients of the 3D attenuation-noise-dose model that are determined for various anatomical regions are retrieved. In step S1160, tube current curves are determined for different anatomical regions, based on the 3D attenuation-noise-dose model, the target noise STD, and the attenuation maps.

The embodiment shown in FIGS. 9 and 11 illustrates a scenario where a 3D surface model is used to represent the relationship among attenuation, image noise, and dose. Alternatively, online tube current modulation can be based on the anatomy-specific look-up tables built in the embodiment shown in FIG. 8. Using patient information from a 3D scout scan, based on the anatomy-oriented 3D surface models or look-up tables, the AEC prediction framework in the present disclosure can achieve more accurate AEC predictions than traditional methods that use 2D radiographic images.

Figure 12:
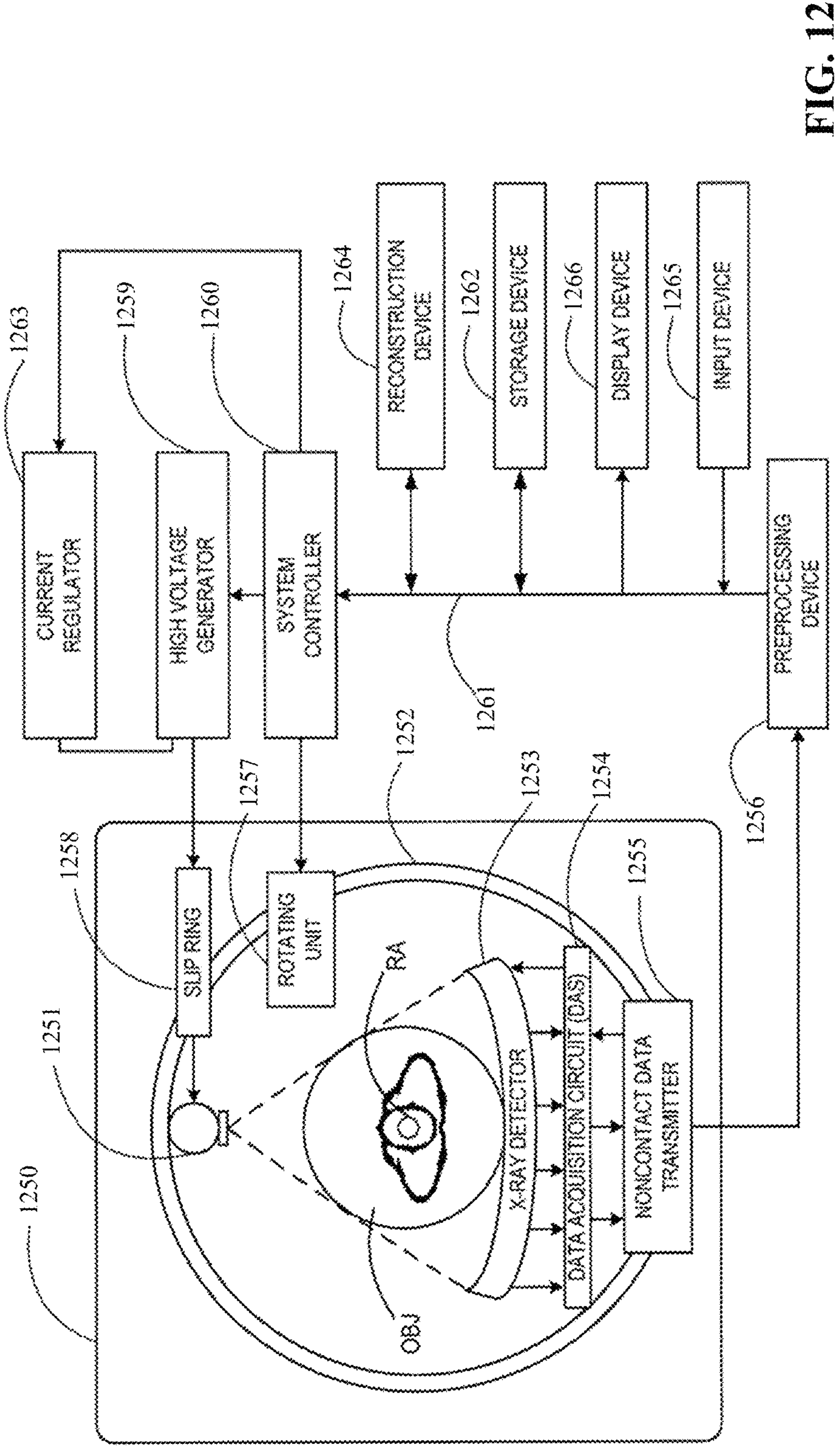
FIG. 12 shows a schematic block diagram of an exemplary CT imaging system that can incorporate the techniques disclosed herein.

FIG. 12 is a schematic block diagram of a CT apparatus or scanner, according to one embodiment of the present disclosure. As shown in FIG. 12, a radiography gantry 1250 is illustrated from a side view and further includes an X-ray tube 1251, an annular frame 1252, and a multi-row or two-dimensional-array-type X-ray detector 1253. The X-ray tube 1251 and X-ray detector 1253 are diametrically mounted across an object OBJ on the annular frame 1252, which is rotatably supported around a rotation axis RA. A rotating unit 1257 rotates the annular frame 1252 at a high speed, such as 0.4 sec/rotation, while the object OBJ is being moved along the axis RA into or out of the illustrated page.

An embodiment of an X-ray CT apparatus according to the present disclosure will be described below with reference to the views of the accompanying drawing. Note that X-ray CT apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present disclosure can be applied to either type. In this case, the rotate/rotate-type, which is currently the mainstream, will be exemplified.

The multi-slice X-ray CT apparatus further includes a high voltage generator 1259 that generates a tube voltage applied to the X-ray tube 1251 through a slip ring 1258 so that the X-ray tube 1251 generates X-rays. The X-rays are emitted towards the object OBJ, whose cross-sectional area is represented by a circle. For example, the X-ray tube 1251 having an average X-ray energy during a first scan that is less than an average X-ray energy during a second scan. Thus, two or more scans can be obtained corresponding to different X-ray energies. The X-ray detector 1253 is located at the opposite side from the X-ray tube 1251 across the object OBJ for detecting the emitted X-rays that have transmitted through the object OBJ. The X-ray detector 1253 further includes individual detector elements or units.

The CT apparatus further includes other devices for processing the detected signals from the X-ray detector 1253. A data acquisition circuit or a Data Acquisition System (DAS) 1254 converts a signal output from the X-ray detector 1253 for each channel into a voltage signal, amplifies the signal, and further converts the signal into a digital signal. The X-ray detector 1253 and the DAS 1254 are configured to handle a predetermined total number of projections per rotation (TPPR).

The above-described data is sent to a preprocessing device 1256, which is housed in a console outside the radiography gantry 1250 through a non-contact data transmitter 1255. The preprocessing device 1256 performs certain corrections, such as sensitivity correction, on the raw data. A memory 1262 stores the resultant data, which is also called projection data at a stage immediately before reconstruction processing. The memory 1262 is connected to a system controller 1260 through a data/control bus 1261, together with a reconstruction device 1264, input device 1265, and display 1266. The system controller 1260 controls a current regulator 1263 that limits the current to a level sufficient for driving the CT system.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 1251 and the X-ray detector 1253 are diametrically mounted on the annular frame 1252 and are rotated around the object OBJ as the annular frame 1252 is rotated about the rotation axis RA. In the fourth-generation geometry system, the detectors are fixedly placed around the patient and an X-ray tube rotates around the patient. In an alternative embodiment, the radiography gantry 1250 has multiple detectors arranged on the annular frame 1252, which is supported by a C-arm and a stand.

The memory 1262 can store the measurement value representative of the irradiance of the X-rays at the X-ray detector unit 1253. Further, the memory 1262 can store a dedicated program for executing the CT image reconstruction, material decomposition, and motion estimation and motion compensation methods including the methods described herein.

The reconstruction device 1264 can execute the above-referenced methods, described herein. Further, reconstruction device 1264 can execute pre-reconstruction processing image processing such as volume rendering processing and image difference processing as needed.

The pre-reconstruction processing of the projection data performed by the preprocessing device 1256 can include correcting for detector calibrations, detector nonlinearities, and polar effects, for example.

Post-reconstruction processing performed by the reconstruction device 1264 can include filtering and smoothing the image, volume rendering processing, and image difference processing, as needed. The image reconstruction process can be performed using filtered back projection, iterative image reconstruction methods, or stochastic image reconstruction methods. The reconstruction device 1264 can use the memory to store, e.g., projection data, reconstructed images, calibration data and parameters, and computer programs.

The reconstruction device 1264 can include a CPU (processing circuitry) that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VDHL, Verilog, or any other hardware description language and the code may be stored in an electronic memory directly within the FPGA or CPLD, or as a separate electronic memory. Further, the memory 1262 can be non-volatile, such as ROM, EPROM, EEPROM or FLASH memory. The memory 1262 can also be volatile, such as static or dynamic RAM, and a processor, such as a microcontroller or microprocessor, can be provided to manage the electronic memory as well as the interaction between the FPGA or CPLD and the memory.

Alternatively, the CPU in the reconstruction device 1264 can execute a computer program including a set of computer-readable instructions that perform the functions described herein, the program being stored in any of the above-described non-transitory electronic memories and/or a hard disc drive, CD, DVD, FLASH drive or any other known storage media. Further, the computer-readable instructions may be provided as a utility application, background daemon, or component of an operating system, or combination thereof, executing in conjunction with a processor, such as a Xeon processor from Intel of America or an Opteron processor from AMD of America and an operating system, such as Microsoft 10, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display 1266. The display 1266 can be an LCD display, CRT display, plasma display, OLED, LED or any other display known in the art.

The memory 1262 can be a hard disk drive, CD-ROM drive, DVD drive, FLASH drive, RAM, ROM or any other electronic storage known in the art.

Numerous modifications and variations of the embodiments presented herein are possible in light of the above teachings. It is therefore to be understood that within the scope of the claims, the application may be practiced otherwise than as specifically described herein. The inventions are not limited to the examples that have just been described; it is in particular possible to combine features of the illustrated examples with one another in variants that have not been illustrated.

Embodiments of the present disclosure may also be as set forth in the following parentheticals.

(1) An apparatus for performing automatic exposure control in a computed tomography (CT) imaging system including an X-ray source, the apparatus comprising processing circuitry configured to acquire helical scan data from a scout scan performed on a first imaging object, determine a target noise standard deviation (STD) for an imaging scan to be performed on the first imaging object after the scout scan, retrieve a pre-stored attenuation-noise-dose relationship relating attenuation of X-rays from the X-ray source that pass through a second imaging object, noise present in reconstructed images of the second imaging object, and tube current values applied to the X-ray source, use the acquired helical scan data and the determined target noise STD to generate a tube current modulation curve, based on the retrieved attenuation-noise-dose relationship, and perform the imaging scan on the first imaging object using the generated tube current modulation curve.

(2) The apparatus of (1), wherein the processing circuitry is further configured to collect scan data from scans performed on the second imaging object under a plurality of different tube current values applied to the X-ray source, develop a particular attenuation-noise-dose relationship based on the collected scan data, and store the developed attenuation-noise-dose relationship, as the pre-stored attenuation-noise-dose relationship.

(3) The apparatus of (2), wherein the developed attenuation-noise-dose relationship is a 3D surface model representing a correlation among attenuation, noise, and tube current values, and the processing circuitry is further configured to: acquire, from the collected scan data, dose information representing the tube current values applied to the X-ray source during the scans performed on the second imaging object, perform anatomy-based segmentation on an image reconstructed from the collected scan data, generate, based on the collected scan data, attenuation maps with respect to the second imaging object, in a slice-by-slice manner, generate, based on the collected scan data, image noise heatmaps in a slice-by-slice manner, based on the anatomy-based segmentation, use the acquired dose information, the generated attenuation maps with respect to the second imaging object, and the generated image noise heatmaps to performing model fitting, so as to determine anatomy-specific coefficients of the 3D surface model, retrieve the 3D surface model with the determined anatomy-specific coefficients, perform anatomy-based segmentation on an image reconstructed from the acquired helical scan data, use the acquired helical scan data to generate attenuation maps with respect to the first imaging object, in a slice-by-slice manner, and based on the retrieved 3D surface model with the determined anatomy-specific coefficients, use the generated attenuation maps with respect to the first imaging object and the determined target noise STD to generate anatomy-specific tube current curves.

(4) The apparatus of (3), wherein the processing circuitry is further configured to perform the anatomy-based segmentation on the image reconstructed from the collected scan data by: performing reconstruction using the collected scan data to generate a reconstructed image, inputting the reconstructed image to a neural network, and obtaining, from an output of the neural network, segmentation labels representing respective anatomies of the second imaging object, as a result of the anatomy-based segmentation.

(5) The apparatus of (4), wherein the processing circuitry is further configured to: obtain a set of training images for training the neural network, obtain, for each specific image of the set of training images, a group of segmentation labels through manual segmentation of the specific image, the segmentation labels representing respective anatomies, and train the neural network, based on the set of training images and the groups of segmentation labels.

(6) The apparatus of (3), wherein the processing circuitry is further configured to generate the attenuation maps with respect to the second imaging object by: performing, based on the collected scan data, analytical reconstruction to obtain 2D reconstructed slices, as the generated attenuation maps, wherein pixels within the obtained 2D reconstructed slices represent linear attenuation coefficients of voxels within the second imaging object.

(7) The apparatus of (3), wherein the processing circuitry is further configured to generate the image noise heatmaps based on the collected scan data by: for each specific scan performed on the second imaging object, splitting scan data collected from the specific scan into a first group of projection data and a second group of projection data, reconstructing a first image based on the first group of projection data, reconstructing a second image based on the second group of projection data, performing, based on the first and second images, a subtraction to generate a difference image, and generating a noise heatmap based on the generated difference image, wherein the generated noise heatmap represents a distribution of noise within a slice reconstructed for the specific scan.

(8) The apparatus of (7), wherein the processing circuitry is further configured to split the scan data collected from the specific scan into a first group including odd projection data and a second group including even projection data.

(9) The apparatus of (2), wherein the developed attenuation-noise-dose relationship is a look-up table representing a correlation among attenuation, noise, and tube current values, and the processing circuitry is further configured to: acquire, from the collected scan data, dose information representing the tube current values applied to the X-ray source during the scans performed on the second imaging object, perform anatomy-based segmentation on an image reconstructed from the collected scan data, generate, based on the collected scan data, attenuation maps with respect to the second imaging object, in a slice-by-slice manner, generate, based on the collected scan data, image noise heatmaps in a slice-by-slice manner, based on the anatomy-based segmentation, use the acquired dose information, the generated attenuation maps with respect to the second imaging object, and the generated image noise heatmaps to create anatomy-specific look-up tables, retrieve the created anatomy-specific look-up tables, perform anatomy-based segmentation on an image reconstructed from the acquired helical scan data, use the acquired helical scan data to generate attenuation maps with respect to the first imaging object, in a slice-by-slice manner, and based on the retrieved anatomy-specific look-up tables, use the generated attenuation maps with respect to the first imaging object and the determined target noise STD to generate anatomy-specific tube current modulation curves.

(10) A method for performing X-ray exposure control in a computed tomography (CT) imaging system including an X-ray source, the method comprising: acquiring helical scan data from a scout scan performed on a first imaging object; determining a target noise standard deviation (STD) for an imaging scan to be performed on the first imaging object after the scout scan; retrieving a pre-stored attenuation-noise-dose relationship relating attenuation of X-rays from the X-ray source that pass through a second imaging object, noise present in reconstructed images of the second imaging object, and tube current values applied to the X-ray source; using the acquired helical scan data and the determined target noise STD to generate a tube current modulation curve, based on the retrieved attenuation-noise-dose relationship; and performing the imaging scan on the first imaging object using the generated tube current modulation curve.

(11) The method of (10), further comprising: collecting scan data from scans performed on the second imaging object under a plurality of different tube current values applied to the X-ray source; developing a particular attenuation-noise-dose relationship based on the collected scan data; and storing the developed attenuation-noise-dose relationship, as the pre-stored attenuation-noise-dose relationship.

(12) The method of (11), wherein the developed attenuation-noise-dose relationship is a 3D surface model representing a correlation among attenuation, noise, and tube current values, the developing step further comprises: acquiring, from the collected scan data, dose information representing the tube current values applied to the X-ray source during the scans performed on the second imaging object, performing anatomy-based segmentation on an image reconstructed from the collected scan data, generating, based on the collected scan data, attenuation maps with respect to the second imaging object, in a slice-by-slice manner, generating, based on the collected scan data, image noise heatmaps in a slice-by-slice manner, and based on the anatomy-based segmentation, using the acquired dose information, the generated attenuation maps with respect to the second imaging object, and the generated image noise heatmaps to performing model fitting, so as to determine anatomy-specific coefficients of the 3D surface model, the step of retrieving the pre-stored attenuation-noise-dose relationship further comprises retrieving the 3D surface model with the determined anatomy-specific coefficients, and the step of generating the tube current modulation prediction further comprises: performing anatomy-based segmentation on an image reconstructed from the acquired helical scan data, using the acquired helical scan data to generate attenuation maps with respect to the first imaging object, in a slice-by-slice manner, and based on the retrieved 3D surface model with the determined anatomy-specific coefficients, using the generated attenuation maps with respect to the first imaging object and the determined target noise STD to generate anatomy-specific tube current modulation curves.

(13) The method of (12), wherein the step of performing the anatomy-based segmentation on the image reconstructed from the collected scan data further comprises: performing reconstruction using the collected scan data to generate a reconstructed image, inputting the reconstructed image to a neural network, and obtaining, from an output of the neural network, segmentation labels representing respective anatomies of the second imaging object, as a result of the anatomy-based segmentation.

(14) The method of (13), further comprising: obtaining a set of training images for training the neural network, obtaining, for each specific image of the set of training images, a group of segmentation labels through manual segmentation of the specific image, the segmentation labels representing respective anatomies, and training the neural network, based on the set of training images and the groups of segmentation labels.

(15) The method of (12), wherein the step of generating the attenuation maps with respect to the second imaging object further comprises: performing, based on the collected scan data, analytical reconstruction to obtain 2D reconstructed slices, as the generated attenuation maps, wherein pixels within the obtained 2D reconstructed slices represent linear attenuation coefficients of voxels within the second imaging object.

(16) The method of (12), wherein the step of generating the image noise heatmaps based on the collected scan data further comprises, for each specific scan performed on the second imaging object, splitting scan data collected from the specific scan into a first group of projection data and a second group of projection data, reconstructing a first image based on the first group of projection data, reconstructing a second image based on the second group of projection data, performing, based on the first and second images, a subtraction to generate a difference image, and generating a noise heatmap based on the generated difference image, wherein the generated noise heatmap represents a distribution of noise within a slice reconstructed for the specific scan.

(17) The method of (16), wherein the splitting step further comprises splitting the scan data collected from the specific scan into a first group including odd projection data and a second group including even projection data.

(18). The method of (11), wherein the developed attenuation-noise-dose relationship is a look-up table representing a correlation among attenuation, noise, and tube current values, the developing step further comprises: acquiring, from the collected scan data, dose information representing the tube current values applied to the X-ray source during the scans performed on the second imaging object, performing anatomy-based segmentation on an image reconstructed from the collected scan data, generating, based on the collected scan data, attenuation maps with respect to the second imaging object, in a slice-by-slice manner, generating, based on the collected scan data, image noise heatmaps in a slice-by-slice manner, and based on the anatomy-based segmentation, using the acquired dose information, the generated attenuation maps with respect to the second imaging object, and the generated image noise heatmaps to create anatomy-specific look-up tables, the step of retrieving the pre-stored attenuation-noise-dose relationship further comprises retrieving the created anatomy-specific look-up tables, and the step of generating the tube current modulation curve further comprises: performing anatomy-based segmentation on an image reconstructed from the acquired helical scan data, using the acquired helical scan data to generate attenuation maps with respect to the first imaging object, in a slice-by-slice manner, and based on the retrieved anatomy-specific look-up tables, using the generated attenuation maps with respect to the first imaging object and the determined target noise STD to generate anatomy-specific tube current modulation curves.

(19) A non-transitory computer readable medium having instructions stored therein that, when executed by one or more processors, cause the one or more processors to perform a method for performing X-ray exposure control in a computed tomography (CT) imaging system including an X-ray source, the method comprising: acquiring helical scan data from a scout scan performed on a first imaging object; determining a target noise standard deviation (STD) for an imaging scan to be performed on the first imaging object after the scout scan; retrieving a pre-stored attenuation-noise-dose relationship relating attenuation of X-rays from the X-ray source that pass through a second imaging object, noise present in reconstructed images of the second imaging object, and tube current values applied to the X-ray source; using the acquired helical scan data and the determined target noise STD to generate a tube current modulation curve, based on the retrieved attenuation-noise-dose relationship; and performing the imaging scan on the first imaging object using the generated tube current modulation curve.

(20) The non-transitory computer readable medium of (19), wherein the method further comprises: collecting scan data from scans performed on the second imaging object under a plurality of different tube current values applied to the X-ray source; developing a particular attenuation-noise-dose relationship based on the collected scan data; and storing the developed attenuation-noise-dose relationship, as the pre-stored attenuation-noise-dose relationship.

Numerous modifications and variations of the embodiments presented herein are possible in light of the above teachings. It is therefore to be understood that within the scope of the claims, the disclosure may be practiced otherwise than as specifically described herein.

What is claimed is:

1. An apparatus for performing automatic exposure control in a computed tomography (CT) imaging system including an X-ray source, the apparatus comprising:
processing circuitry configured to
acquire helical scan data from a scout scan performed on a first imaging object,
determine a target noise standard deviation (STD) for an imaging scan to be performed on the first imaging object after the scout scan,
retrieve a pre-stored attenuation-noise-dose relationship relating attenuation of X-rays from the X-ray source that pass through a second imaging object, noise present in reconstructed images of the second imaging object, and tube current values applied to the X-ray source,
use the acquired helical scan data and the determined target noise STD to generate a tube current modulation curve, based on the retrieved attenuation-noise-dose relationship, and
perform the imaging scan on the first imaging object using the generated tube current modulation curve.

2. The apparatus of claim 1, wherein the processing circuitry is further configured to:
collect scan data from scans performed on the second imaging object under a plurality of different tube current values applied to the X-ray source,
develop a particular attenuation-noise-dose relationship based on the collected scan data, and
store the developed attenuation-noise-dose relationship, as the pre-stored attenuation-noise-dose relationship.

3. The apparatus of claim 2, wherein the developed attenuation-noise-dose relationship is a 3D surface model representing a correlation among attenuation, noise, and tube current values, and the processing circuitry is further configured to:
acquire, from the collected scan data, dose information representing the tube current values applied to the X-ray source during the scans performed on the second imaging object,
perform anatomy-based segmentation on an image reconstructed from the collected scan data,
generate, based on the collected scan data, attenuation maps with respect to the second imaging object, in a slice-by-slice manner,
generate, based on the collected scan data, image noise heatmaps in a slice-by-slice manner,
based on the anatomy-based segmentation, use the acquired dose information, the generated attenuation maps with respect to the second imaging object, and the generated image noise heatmaps to performing model fitting, so as to determine anatomy-specific coefficients of the 3D surface model,
retrieve the 3D surface model with the determined anatomy-specific coefficients,
perform anatomy-based segmentation on an image reconstructed from the acquired helical scan data,
use the acquired helical scan data to generate attenuation maps with respect to the first imaging object, in a slice-by-slice manner, and
based on the retrieved 3D surface model with the determined anatomy-specific coefficients, use the generated attenuation maps with respect to the first imaging object and the determined target noise STD to generate anatomy-specific tube current curves.

4. The apparatus of claim 3, wherein the processing circuitry is further configured to perform the anatomy-based segmentation on the image reconstructed from the collected scan data by:
performing reconstruction using the collected scan data to generate a reconstructed image,
inputting the reconstructed image to a neural network, and
obtaining, from an output of the neural network, segmentation labels representing respective anatomies of the second imaging object, as a result of the anatomy-based segmentation.

5. The apparatus of claim 4, wherein the processing circuitry is further configured to:
obtain a set of training images for training the neural network,
obtain, for each specific image of the set of training images, a group of segmentation labels through manual segmentation of the specific image, the segmentation labels representing respective anatomies, and
train the neural network, based on the set of training images and the groups of segmentation labels.

6. The apparatus of claim 3, wherein the processing circuitry is further configured to generate the attenuation maps with respect to the second imaging object by:
performing, based on the collected scan data, analytical reconstruction to obtain 2D reconstructed slices, as the generated attenuation maps, wherein pixels within the obtained 2D reconstructed slices represent linear attenuation coefficients of voxels within the second imaging object.

7. The apparatus of claim 3, wherein the processing circuitry is further configured to generate the image noise heatmaps based on the collected scan data by:

for each specific scan performed on the second imaging object, splitting scan data collected from the specific scan into a first group of projection data and a second group of projection data, reconstructing a first image based on the first group of projection data, reconstructing a second image based on the second group of projection data, performing, based on the first and second images, a subtraction to generate a difference image, and generating a noise heatmap based on the generated difference image, wherein the generated noise heatmap represents a distribution of noise within a slice reconstructed for the specific scan.

8. The apparatus of claim 7, wherein the processing circuitry is further configured to split the scan data collected from the specific scan into a first group including odd projection data and a second group including even projection data.

9. The apparatus of claim 2, wherein the developed attenuation-noise-dose relationship is a look-up table representing a correlation among attenuation, noise, and tube current values, and the processing circuitry is further configured to:

acquire, from the collected scan data, dose information representing the tube current values applied to the X-ray source during the scans performed on the second imaging object, perform anatomy-based segmentation on an image reconstructed from the collected scan data, generate, based on the collected scan data, attenuation maps with respect to the second imaging object, in a slice-by-slice manner, generate, based on the collected scan data, image noise heatmaps in a slice-by-slice manner, based on the anatomy-based segmentation, use the acquired dose information, the generated attenuation maps with respect to the second imaging object, and the generated image noise heatmaps to create anatomy-specific look-up tables, retrieve the created anatomy-specific look-up tables, perform anatomy-based segmentation on an image reconstructed from the acquired helical scan data, use the acquired helical scan data to generate attenuation maps with respect to the first imaging object, in a slice-by-slice manner, and based on the retrieved anatomy-specific look-up tables, use the generated attenuation maps with respect to the first imaging object and the determined target noise STD to generate anatomy-specific tube current modulation curves.

10. A method for performing X-ray exposure control in a computed tomography (CT) imaging system including an X-ray source, the method comprising:

acquiring helical scan data from a scout scan performed on a first imaging object;

determining a target noise standard deviation (STD) for an imaging scan to be performed on the first imaging object after the scout scan;

retrieving a pre-stored attenuation-noise-dose relationship relating attenuation of X-rays from the X-ray source that pass through a second imaging object, noise present in reconstructed images of the second imaging object, and tube current values applied to the X-ray source;

using the acquired helical scan data and the determined target noise STD to generate a tube current modulation curve, based on the retrieved attenuation-noise-dose relationship; and performing the imaging scan on the first imaging object using the generated tube current modulation curve.

11. The method of claim 10, further comprising:

collecting scan data from scans performed on the second imaging object under a plurality of different tube current values applied to the X-ray source;

developing a particular attenuation-noise-dose relationship based on the collected scan data; and storing the developed attenuation-noise-dose relationship, as the pre-stored attenuation-noise-dose relationship.

12. The method of claim 11, wherein the developed attenuation-noise-dose relationship is a 3D surface model representing a correlation among attenuation, noise, and tube current values, the developing step further comprises:

acquiring, from the collected scan data, dose information representing the tube current values applied to the X-ray source during the scans performed on the second imaging object, performing anatomy-based segmentation on an image reconstructed from the collected scan data, generating, based on the collected scan data, attenuation maps with respect to the second imaging object, in a slice-by-slice manner, generating, based on the collected scan data, image noise heatmaps in a slice-by-slice manner, and based on the anatomy-based segmentation, using the acquired dose information, the generated attenuation maps with respect to the second imaging object, and the generated image noise heatmaps to performing model fitting, so as to determine anatomy-specific coefficients of the 3D surface model, the step of retrieving the pre-stored attenuation-noise-dose relationship further comprises retrieving the 3D surface model with the determined anatomy-specific coefficients, and the step of generating the tube current modulation prediction further comprises:

performing anatomy-based segmentation on an image reconstructed from the acquired helical scan data, using the acquired helical scan data to generate attenuation maps with respect to the first imaging object, in a slice-by-slice manner, and based on the retrieved 3D surface model with the determined anatomy-specific coefficients, using the generated attenuation maps with respect to the first imaging object and the determined target noise STD to generate anatomy-specific tube current modulation curves.

13. The method of claim 12, wherein the step of performing the anatomy-based segmentation on the image reconstructed from the collected scan data further comprises:

performing reconstruction using the collected scan data to generate a reconstructed image, inputting the reconstructed image to a neural network, and obtaining, from an output of the neural network, segmentation labels representing respective anatomies of the second imaging object, as a result of the anatomy-based segmentation.

14. The method of claim 13, further comprising:

obtaining a set of training images for training the neural network, obtaining, for each specific image of the set of training images, a group of segmentation labels through manual segmentation of the specific image, the segmentation labels representing respective anatomies, and training the neural network, based on the set of training images and the groups of segmentation labels.

15. The method of claim 12, wherein the step of generating the attenuation maps with respect to the second imaging object further comprises:

performing, based on the collected scan data, analytical reconstruction to obtain 2D reconstructed slices, as the generated attenuation maps, wherein pixels within the obtained 2D reconstructed slices represent linear attenuation coefficients of voxels within the second imaging object.

16. The method of claim 12, wherein the step of generating the image noise heatmaps based on the collected scan data further comprises, for each specific scan performed on the second imaging object, splitting scan data collected from the specific scan into a first group of projection data and a second group of projection data, reconstructing a first image based on the first group of projection data, reconstructing a second image based on the second group of projection data, performing, based on the first and second images, a subtraction to generate a difference image, and generating a noise heatmap based on the generated difference image, wherein the generated noise heatmap represents a distribution of noise within a slice reconstructed for the specific scan.

17. The method of claim 16, wherein the splitting step further comprises splitting the scan data collected from the specific scan into a first group including odd projection data and a second group including even projection data.

18. The method of claim 11, wherein the developed attenuation-noise-dose relationship is a look-up table representing a correlation among attenuation, noise, and tube current values, the developing step further comprises:

acquiring, from the collected scan data, dose information representing the tube current values applied to the X-ray source during the scans performed on the second imaging object, performing anatomy-based segmentation on an image reconstructed from the collected scan data, generating, based on the collected scan data, attenuation maps with respect to the second imaging object, in a slice-by-slice manner, generating, based on the collected scan data, image noise heatmaps in a slice-by-slice manner, and based on the anatomy-based segmentation, using the acquired dose information, the generated attenuation maps with respect to the second imaging object, and the generated image noise heatmaps to create anatomy-specific look-up tables, the step of retrieving the pre-stored attenuation-noise-dose relationship further comprises retrieving the created anatomy-specific look-up tables, and the step of generating the tube current modulation curve further comprises:

performing anatomy-based segmentation on an image reconstructed from the acquired helical scan data, using the acquired helical scan data to generate attenuation maps with respect to the first imaging object, in a slice-by-slice manner, and based on the retrieved anatomy-specific look-up tables, using the generated attenuation maps with respect to the first imaging object and the determined target noise STD to generate anatomy-specific tube current modulation curves.

19. A non-transitory computer readable medium having instructions stored therein that, when executed by one or more processors, cause the one or more processors to perform a method for performing X-ray exposure control in a computed tomography (CT) imaging system including an X-ray source, the method comprising:

acquiring helical scan data from a scout scan performed on a first imaging object;

determining a target noise standard deviation (STD) for an imaging scan to be performed on the first imaging object after the scout scan;

retrieving a pre-stored attenuation-noise-dose relationship relating attenuation of X-rays from the X-ray source that pass through a second imaging object, noise present in reconstructed images of the second imaging object, and tube current values applied to the X-ray source;

using the acquired helical scan data and the determined target noise STD to generate a tube current modulation curve, based on the retrieved attenuation-noise-dose relationship; and performing the imaging scan on the first imaging object using the generated tube current modulation curve.

20. The non-transitory computer readable medium of claim 19, wherein the method further comprises:

collecting scan data from scans performed on the second imaging object under a plurality of different tube current values applied to the X-ray source;

developing a particular attenuation-noise-dose relationship based on the collected scan data; and storing the developed attenuation-noise-dose relationship, as the pre-stored attenuation-noise-dose relationship.

* * * * *